United States Patent [19]

Cornell et al.

[11] Patent Number: 4,580,565

[45] Date of Patent: * Apr. 8, 1986

[54] LANCET INJECTOR

[75] Inventors: William D. Cornell, Ballwin; Carnot Evans, St. Louis, both of Mo.

[73] Assignee: Sherwood Medical Company, St. Louis, Mo.

[*] Notice: The portion of the term of this patent subsequent to Mar. 12, 2002 has been disclaimed.

[21] Appl. No.: 709,017

[22] Filed: Mar. 7, 1985

Related U.S. Application Data

[63] Continuation of Ser. No. 483,074, Apr. 7, 1983, Pat. No. 4,503,856, which is a continuation of Ser. No. 278,024, Jun. 29, 1981, Pat. No. 4,379,456.

[51] Int. Cl.$^4$ ............................................. A61B 17/32
[52] U.S. Cl. .................................................. 128/314
[58] Field of Search ................ 128/314, 333, 329, 315

[56] References Cited

U.S. PATENT DOCUMENTS 4,379,456 4/1983 Cornell et al. ........................ 128/314
4,503,856 3/1985 Cornell et al. ........................ 128/314

Primary Examiner—John D. Yasko
Attorney, Agent, or Firm—Stanley N. Garber; Andrew J. Beck; William R. O'Meara

[57] ABSTRACT

A lancet injector is provided which has a tubular housing, a slidable lancet holder in the housing, a compression spring connected between the holder and one end of the housing, and a holder control member extending through a longitudinal slot in the sidewall of the housing. The control member is operable to move the lancet holder to a latched retracted position against the force of the spring, release the holder so that it moves linearly under the force of the spring and inertia to a skin piercing position and then back to a neutral position in which the spring is in a free length condition.

19 Claims, 6 Drawing Figures

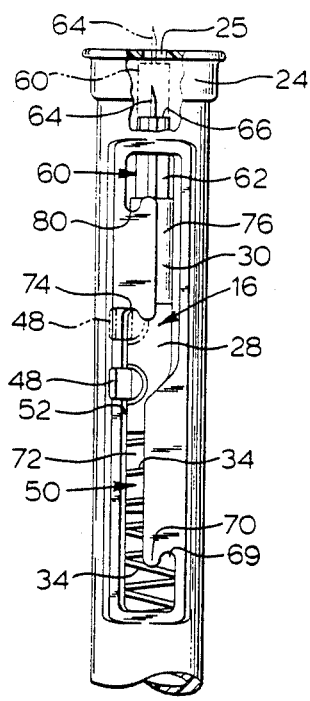
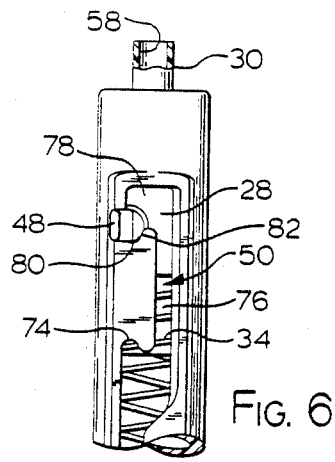
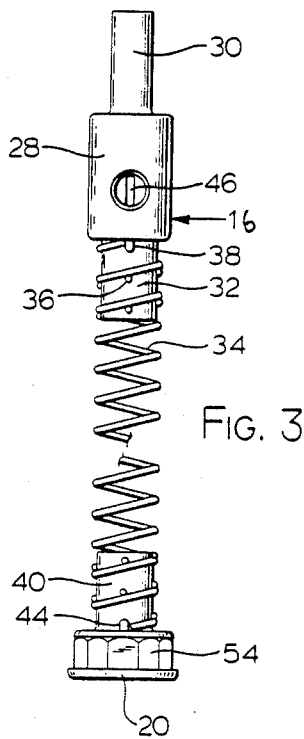
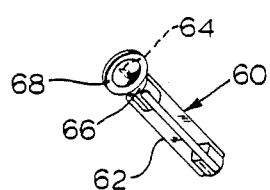
FIG. 5
FIG. 6
FIG. 3
FIG. 4

LANCET INJECTOR

This is a continuation of application Ser. No. 483,074 filed on Apr. 7, 1983 now U.S. Pat. No. 4,503,856, which is a continuation of Ser. No. 278,024 filed on June 29, 1981 now U.S. Pat. No. 4,379,456.

DESCRIPTION

1. Technical Field

This invention relates to lancet injectors and more particularly to an injector adapted for use with single-use or disposable lancets for obtaining blood samples for test purposes.

2. Background Art

Lancets generally have a handle and a needle extending from one end. The lancet may be grasped between the thumb and index finger and made to pierce the skin, for example, the skin of a patient's finger. The lancet is removed from the incision and blood from the finger transferred to a blood collection tube, such as a capillary tube or a pipette, for clinical testing. Some problems are associated with such a procedure. For example, the depth of penetration, the force employed in making the incision, and the angle of insertion and removal vary in accordance with the person using the procedure. Also, the person or patient may be able to view the lancet or procedure performed and this may be undesirable in some cases.

In attempting to overcome one or more of the above problems or disadvantages, spring actuated lancet injector devices have been made, however, they have not been entirely satisfactory. For example, some have been relatively complicated in construction and expensive to make. Some constructions require a plurality of springs and a relatively large number of elements for performing such functions as driving, latching and retracting the lancet. Also, in some cases the lancet is in view and this may add to the anxiety of the patient, especially where the incision is self-made, for example, when a diabetic makes blood glucose tests at home.

DISCLOSURE OF THE INVENTION

It is therefore an object of the present invention to provide an improved blood lancet injector which is relatively economical, simple and effective in use, and which substantially overcomes one or more of the above problems.

In accordance with one aspect of the present invention, a lancet holder and a spring are disposed in a housing. An external control member is connected to the holder to move the holder to a retracted position against the force of the spring. The control member is movable to release the holder to allow the holder to move to a lancet skin piercing position and then to a withdrawn position. In another aspect, a single spring is used.

These as well as other objects and advantages of the present invention will become more apparent from the following detailed description and accompanying drawing.

BRIEF DESCRIPTION OF THE DRAWINGS

FIG. 3 is an elevational view of an assembly of parts employed in the injector device of FIG. 1;

FIG. 4 is a perspective view of the lancet of FIG. 1;

FIG. 5 is a fragmentary elevational view showing the upper portion of the injector device of FIG. 1 and illustrating the lancet in phantom in its skin piercing position, and the lancet and holder in the neutral position; and FIG. 6 is a fragmentary elevational view of the upper portion of the injector device of FIG. 1 but showing the lancet holder in its lancet holding and unloading position with the lancet removed from the device.

DETAILED DESCRIPTION OF THE PREFERRED EMBODIMENT

Figure 1:
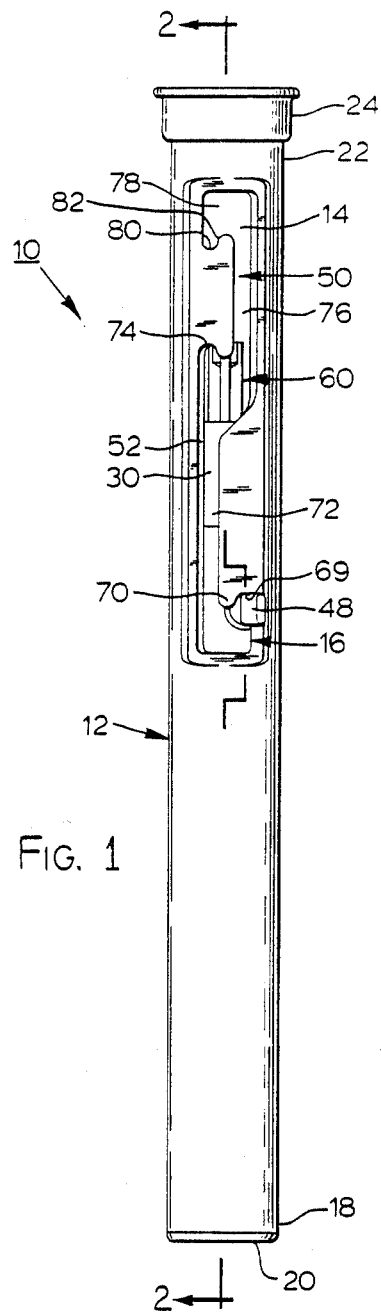
FIG. 1 is an elevational view of a lancet injector device in accordance with a preferred embodiment of the invention.
Figure 2:
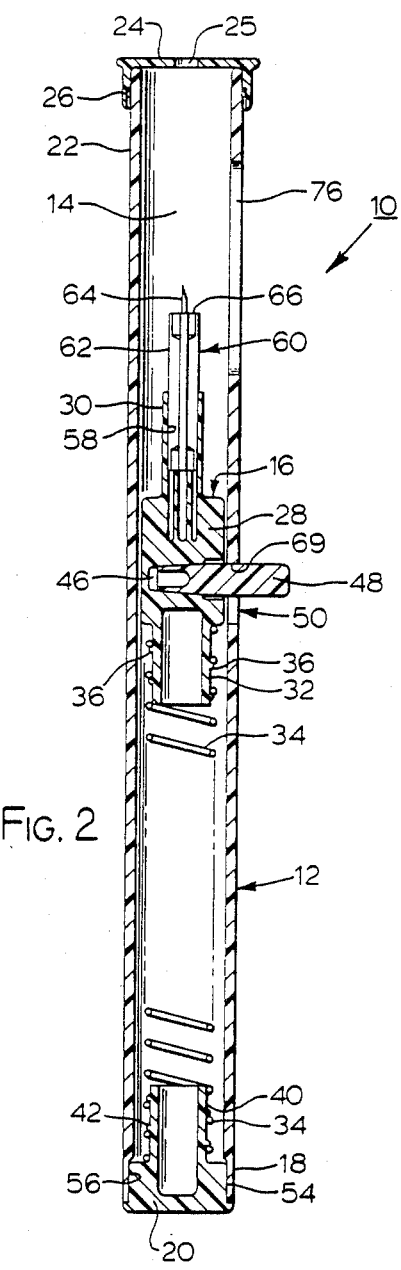
FIG. 2 is a cross-sectional view of the injector device of FIG. 1.

Referring now to the drawings, and particularly to FIGS. 1 and 2, a lancet injector 10 is shown including an elongate, generally cylindrical, housing 12 having a chamber or bore 14 and a lancet holder 16 slidable in the housing bore 14. Housing 12 has a proximal end 18 in which is secured an end plug 20, and a distal end 22 covered by a removable cap 24 having a central opening 25. Cap 24 is frictionally held in place by an annular bead 26 on the exterior of housing 12. In this way, the cap 24 can be snapped on and off the distal end 22 of the housing.

The lancet holder 16, as also seen in FIG. 3, includes a generally cylindrical portion or slide 28 having a lancet holding member 30 integrally connected to the distal end of the slide and a cylindrical extension or spring connector 32 at the proximal end of the slide. A spring 34, shown as a coil spring, is disposed in the bore 14 between the holder 16 and the plug 20. Spring 34 is shown engaged between the holder and a lower end portion of the housing. The connector 32 is provided with a series of external integral bumps 36 disposed in a spiral arrangement for threadedly receiving and holding the upper or distal end of coil spring 34. The spring 34 is threaded onto connector 32 until the end of the spring engages an integral stop bump 38. The end plug 20 is shown provided with an integral extension or spring connector 40 having a spiral series of integral bumps 42 which threadedly receives and, as shown, holds the lower end of coil spring 34. The spring 34 is threaded onto connector 40 until the end of the spring engages an integral stop bump 44. If desired, the spring connectors 32 and 40 may be provided with suitable screw threads instead of the series of bumps or the ends of the spring 34 may be fixed to those connectors by other suitable means.

The slide 28 has a hole 46 in which is secured a manual slide control member or control latch 48 which extends through a slot, indicated generally at 50, in the sidewall of the housing 12. latch 48 extends to the exterior of the housing so that it provides an exterior manual control movable along the slot 50 for positioning the lancet holder 16 in a number of positions, as will be further described.

In assembling the device 10, the opposite ends of spring 34 may be respectively threaded onto connectors 32 and 40 to provide unitary assembly, as seen in FIG. 3. This assembly can be inserted into the proximal end of the housing 12. The free length of the spring 34 is such that the unit may be manually rotated in the housing 12 by rotating plug 20 until the hole 46 appears in the slot 50. The latch 48 may then be inserted through the slot and into hole 46. The latch 48 is fixed in the hole 46, for example, it may be adhesively connected or solvent bonded to the sidewalls of hole 46.

The holder 16 and connected latch 48 are preferably spring biased in a counterclockwise direction of rotation, as viewed in the drawings, that is arcuately toward engagement with the left sidewall 52 of slot 50. This may be accomplished by providing the plug 20 and inner wall of the housing 12 at its proximal end with cooperating surfaces which permit insertion of the plug in a selected relative position with respect to slide 28. For example, as shown in FIG. 3, the plug 20 is provided with a plurality flats 54 which register with a plurality of flats 56 (FIG. 2) on the inner sidewall of bore 14 at the proximal end 18. In this way, after the latch 48 is secured in hole 46, the plug 20 can be rotated counterclockwise so that the latch 48 engages a wall of slot 50, and then the plug 20 is further rotated in the same direction a slight amount relative to holder 16, and then the plug is inserted into the end 18 of the housing. Because of the cooperating flats 54 and 56, the plug cannot rotate and remains in its inserted position with the spring 34 resiliently biasing the holder 16 and latch 48 leftwardly or counterclockwise toward the left edge 52 of slot 50. The plug 20 may be adhesively connected such as by applying a suitable adhesive to the plug prior to insertion or a suitable solvent where the plug and housing materials can be solvent bonded.

The lancet holding member 30 is shown as a sleeve or cylindrical barrel having inner sidewalls 58 which frictionally engage outer peripheral surfaces of a lancet 60. The lancet 60 is shown including a base or handle 62, such as of plastic material, and a needle 64, such as a solid stainless steel pointed needle. The handle 62 may be molded about the needle so that the tip of the needle extends outwardly beyond the upper end 66 of the handle. In FIG. 4, the lancet 60 is shown including an integrally molded needle cap or sheath 68 covering the pointed needle tip. The connection between the sheath 68 and the handle 62 is fragile so that by twisting or rotating the sheath relative to the handle, and then pulling the sheath from the needle tip, the needle tip is exposed. The depth of the lancet holding member 30 is less than the length of the lancet handle 62 so that the upper portion, such as its upper one half, extends out of the holder and may be grasped, for example, between the thumb and finger, for inserting the lancet 60 into the holder 30 and for removing it after use. The bottom of the lancet bottoms on the bottom of the member 30 as shown in FIG. 2.

The slot 50, as best seen in FIGS. 1, 2 and 5, is shaped so as to have a relative wide portion at the proximal end of the slot through which the control member 48 can be moved. In FIGS. 1 and 2, the member 48 is shown in its retracted position which places holder 16, member 30, and lancet 60 in the retracted position with the needle tip wholly within the housing 12. The control member 48 is shown releasably latched in an axial recess 69 having a downward protrusion 70 for securely holding the lancet holder in the retracted position. When the lancet holder 30 is in the retracted position, the spring 30 is in compression and exerting maximum longitudinal or linear spring force on the holder 16 in the distal direction. Also, the holder 16 is held in recess 69 against the biasing force of spring 34.

When the control member 49 is manually unlatched from the retracted position (FIGS. 1 and 2), such as by moving it leftward over the protrusion 70 by applying pressure with a finger or thumb, the holder 16, due to the force of spring 34 and inertia, moves swiftly linearly or longitudinally and distally through housing bore 14 to a skin piercing position wherein the point of needle 64 extends through opening 25 in the end cap 24 and distally of the distal end of the housing as shown in phantom in FIG. 5. During this movement control member 48 moves along a slot portion 72. The holder 16 and lancet 60 are quickly linearly retracted to a neutral position, that is, with the point of needle 64 retracted or withdrawn from the incision and within the housing 12 as shown in FIG. 5. Spring 34 is sized relative to housing 12 such that when the holder 16 and control member 48 are in this neutral position, the spring 34 is at its free length position or neutral force position, that is, spring 34 is substantially neither in tension or compression.

In moving from the retracted position of FIG. 1 to the skin penetrating position shown in phantom in FIG. 5, it is primarily the inertia or momemtum of the moving holder 16 that causes the lancet to move distally past the neutral position of the holder or free length position of the distal end of spring 34 (position shown in full in FIG. 5). Since the distal end of spring 34 is extended distally beyond the position it would have when the spring 34 in its neutral or free length condition due primarily to the inertia of the moving holder 16, the spring is tensioned and therefore swiftly retracts or moves the needle point proximally from the piercing position back to the neutral position.

The parts may be proportioned such that the extent of distal travel of the lancet 60 may be limited by the engagement of the control member 48 with a sidewall 74 (FIGS. 1, 5 and 6) of the slot 50, the indicated phantom position of member 48 in FIG. 5, or, if desired, by the engagement of the upper end 66 of the lancet handle with the inner side of the end wall of cap 24. In some cases, the construction may allow the end 66 to strike the skin.

The holder 16 and lancet holder 30 may be moved to a lancet access or unloading and loading position, the position shown in FIG. 6. This is accomplished by removing cap 24 and urging the control member 48 rightwardly against the bias force from its neutral position of FIG. 5 and into an elongate slot portion 76 of slot 50, then longitudinally or linearly upwardly and distally into an enlarged slot portion 78, and then leftwardly into the access position in a recess 80 in slot 50 and which has a distally extending sidewall 82 holding the member 48 in place. During this distal movement in slot portion 76 the coil spring 34 is tensioned, that is, stretched beyond its neutral or free length condition of FIG. 5. The tensioned spring 34 tends to maintain the member 48 urged downwardly in groove 80 so that it cannot move out of the groove.

In the lancet access condition of holder 16, as shown in FIG. 6, the lancet holding member 30 extends through and above the upper or distal open end of the housing 12. In this position the upper portion of the lancet 60 may be grasped by the handle 62 and pulled upwardly to remove it from the member 30. A new lancet may then be inserted into the holder 30 until it bottoms against the inner bottom wall of the member 30. After a new lancet is inserted into the holding member in the access position of FIG. 6, the needle sheath such as sheath 68 (FIG. 4) is removed to expose the pointed needle tip, and then the external control member 48 is manually moved out of recess 80 into the enlarged slot portion 78. The member 48 is moved rightwardly against the rotary bias force of spring 34 into an elongate slot 76 where the force of tensioned spring 34 swiftly moves the slide 28 proximally longitudinally or axially of the housing so that it moves back into its neutral position shown in FIG. 5, the bias force of the spring urging it against the left edge 52 of the slot 50. The cap 24 may then be snapped back onto the distal end of housing 12.

In use, a new lancet, such as lancet 60, is inserted into the lancet holder 30 when the control member 48 is positioned in the lancet access position indicated in FIG. 6. The needle sheath, such as sheath 68 (FIG. 4) is removed from the lancet, and the control member 48 is manually moved out of recess 80 so that the tensioned spring 34 withdraws the lancet and slide 48 through slot portion 76 to the neutral position indicated in FIG. 5. The cap 24 or a new cap may now be placed over the distal end of the housing 12.

Next, the control member 48 is manually moved proximally or downwardly in slot portion 72 compressing coil spring 34 and then over to recess 68 to place the member 48 and holder 16 in a latched retracted or cocked position as shown in FIGS. 1 and 2. The housing 12 may now be hand grasped and the end cap 24 pressed against the skin, such as the skin of the finger, of the person whose blood is to be tested. The control member 48 may now be forced out of the retracted position so that the force of spring 34 and the inertia of the lancet 60 and lancet holder 16 effect piercing of the skin by the needle tip of the lancet and quick removal of the needle from the skin incision to the neutral position as indicated in FIG. 5. The cap 24 may now be removed and the control member 48 moved to the lancet access position as shown in FIG. 6 so that the used lancet may be easily and safely removed from the injector 10 and discarded. At this time, a new lancet may be inserted into the holding member 30 and the control member again moved to the neutral position of FIG. 5 so that the device is again ready to be used to effect skin piercing.

The blood flow caused by the lancet piercing the skin may be collected in a capillary tube or pipette and subjected to clinical testing. For example, at times, glucose testing may be done relatively often in the case of diabetics. Also, such testing may be self-performed such as in the home for monitoring blood glucose.

The lancet injector device 10 effects a very quick incision and withdrawal of the lancet needle so that patient discomfort is minimized. Since the lancet is substantially hidden by the housing, one does not see the lancet point during use and the anxiety of the patient is generally substantially less than where one sees the lancet point. Also, the injector 10 is easy to operate.

The injector 10 requires only one functional spring while operating in a simple and highly effective manner. The spring 34 is shown as a single coil propulsion compression spring which propels the lancet holder 16 for the skin piercing operation. Spring 34 provides the force for piercing the skin as well as swiftly withdrawing the lancet from the incision. The spring 34 is also tensioned when the device is in its lancet access position (FIG. 6) so that its force is also used to quickly withdraw the exposed lancet needle to the neutral position (FIG. 5) when the control member 48 is moved accordingly. Also, spring 34 provides the arcuate biasing force normally urging the slide 48 leftwardly when such bias is employed in the device. The construction of device 10 requires few moving parts and, in general, is simple and economical to make and use.

The housing 12, holder 16 and plug 20 may be economically molded from any suitable plastic, for example, from a copolymer made from acrylonitrile, butadiene, and styrene (ABS), or polypropylene. The cap 24 may also be made from a suitable plastic such as polypropylene. While a snap-on type cap 24 is shown, other cap constructions allowing attachment and removal are possible.

As various changes could be made in the above construction without departing from the scope of the invention, it is intended that all matter contained in the above description and apparatus shown in the accompanying drawing shall be interpreted as illustrative and not in a limiting sense.

We claim:

1. A lancet injector comprising an elongate housing having an elongate chamber therein, a lancet holder adapted to hold a lancet slidable longitudinally of said chamber, spring means in said chamber, a slot in the sidewall of said housing extending generally longitudinally of said housing, a control member connected to said holder and extending through said slot to the exterior of said housing, said control member being movable to a latched retracted position in said slot to thereby move said holder against the force of said spring means to a retracted position within said chamber, said control member being movable from said latched retracted position so that the force of spring means effects distal movement of said holder longitudinally to a lancet skin piercing position, said control member being distally movable longitudinally in said slot beyond said skin piercing position to a latched lancet access position wherein said holder can be loaded with a lancet.

2. The injector of claim 1 wherein said holder extends outwardly of the distal end of said housing when in said access position.

3. The injector of claim 2 wherein said holder includes a sleeve for frictionally receiving a portion of a lancet.

4. A lancet injector comprising an elongate housing having a generally longitudinally extending slot in the sidewall thereof, a lancet holder longitudinally slidable in said housing and adapted to releaseably receive a lancet for piercing the skin, spring means in said housing, and a control member extending through said slot and connected to said holder for manually moving said holder, said control member being movable to move said holder linearly in a proximal direction against the force of said spring means to a releasable retracted position, said control member being movable to release said holder from said retracted position so that the force of said spring means and the inertia of said holder during movement thereof moves said holder linearly in a distal direction to a lancet piercing position in which said spring means is adapted to move said holder proximally from said piercing position to a neutral position where said spring means is in a free length neutral force condition, said control member being distally movable to move said holder to a lancet access position distally beyond said neutral position.

5. The injector of claim 4 wherein said slot includes a first recess for receiving said control member and holding it and said holder against the force of said spring means thereby latching said holder in the retracted position, and a second recess for receiving said control member and holding it and said holder against the force of said spring means for latching said holder in said lancet access position.

6. The injector of claim 4 or 5 wherein the distal end of said holder is distally beyond the distal end of said housing when said holder is in said lancet access position.

7. The injector of claim 4 and 5 wherein said spring means is a coil spring and the sole functional spring in the injector.

8. The injector of claim 4 or 5 wherein said slot includes a longitudinally extending slot portion connected at the proximal end with said first slot recess and having a wall at the distal end thereof, said control member being engageable with said wall to limit the distal movement of said holder after release thereof from said retracted position and defines said lancet piercing position when said control member is engaged with said wall, said holder being movable from said piercing position to a neutral force position wherein said spring means is in the free length neutral force condition and proximal of said wall.

9. The injector of claim 21 wherein said slot includes a second longitudinally extending slot portion connected with said first named slot portion and said second recess, and said spring means is arranged to bias said holder in a rotary direction.

10. The lancet injector comprising an elongate housing having an elongate chamber therein, a lancet holder linearly slideable longitudinally in said chamber and adapted to hold a lancet, spring means in said chamber, a slot in the sidewall of said housing extending generally longitudinally of said housing and having first and second recesses, a control member connected to said holder and extending through said slot to the exterior of said housing for manually moving said holder, said control member being movable to a latched retracted position into said first recess to thereby move said holder against the force of said spring means to a retracted position within said chamber wherein force acting in one direction is stored in said spring means, said control member being movable from said latched retracted position in said first recess so that the force of said spring means effects linear distal movement of said holder and control member longitudinally to lancet skin piercing positions, said control member being distally movable longitudinally in said slot distally beyond its skin piercing position to a latched lancet access postiion in said second recess wherein force acting in the opposite direction is stored in said spring means and said holder is held against longitudinal movement by walls of said second recess and wherein said holder can be loaded with a lancet.

11. The injector of claim 10 wherein said holder extends distally outwardly of the distal end of said housing when said control member is in said access position.

12. The injector of claim 10 or 11 wherein said spring means is fixedly secured at its opposite ends to said holder and a portion of said housing, respectively.

13. A lancet injector comprising an elongate housing, a lancet holder longitudinally slideable linearly in said housing and adapted to have a lancet releaseably connected thereto, a coil spring in said housing fixedly connected at one end to said holder and fixedly connected at the opposite end to a portion of said housing, said housing having an opening through the sidewall thereof, a manually operated control member connected to said holder and extending through said opening to the exterior of said housing for controlling the movement of said holder, said housing opening having sidewalls defining first and second longitudinally extending slots, said first slot being connected to and extending distally beyond said second slot, said second slot having a distal end wall, said sidewalls also defining a first recess disposed arcuately relative to said second slot and connected thereto, and a second recess adjacent to the distal end of said first slot and connected to and spaced arcuately relative thereto, said control member being in a neutral position proximally of said distal end wall of said second slot when said spring is in its neutral force condition, said control member being movable proximally in said second slot from said neutral position into said first recess to thereby latch said holder in a retracted position with said spring urging said control member in a distal direction toward said first recess, said holder being movable under the forces of said spring from said retracted position in response to movement of said control member from said first recess to momentarily move said holder from said retracted position and said control member distally in said second slot to skin piercing positions in which the distal tip of a lancet when connected to said holder is moved distally of the distal end of said housing for piercing the skin of a patient when disposed adjacent the distal end of the housing, said control member being movable distally beyond said neutral position and engageable with said distal end wall of said second slot to limit the distal movement of said holder, said control member being movable from said neutral position thereof distally and linearly in said first slot and then into said second recess to thereby latch said holder in a lancet access position wherein a lancet may be inserted and removed said said holder, said spring being adapted when said control member is in said second recess to urge said control member in a proximal direction towards said second recess.

14. The injector of claim 13 wherein said spring applies a rotary biasing force against said holder, and said spring is the only functional spring in the injector.

15. The injector of claim 4, 5, 11 or 13 further including an end cap removably connectable to the distal end of said housing and having an opening for movement therethrough of a needle point of a lancet connected to said holder during a skin piercing operation.

16. The injector of claim 4, 5, 11 or 13 further including a lancet having a handle and a needle point extending from the distal end of said handle, and wherein said holder includes a sleeve having an open distal end for slidingly receiving said handle in frictional engagement with the sidewalls of said sleeve.

17. The injector of claim 1 including a lancet having an elongate body and a needle with a painted distal tip connected to said body, said body being frictionally engageable and slidable into and out of said holder.

18. The injector of claim 17, 5, 13 and 14 wherein said lancet access position of said holder is distally beyond said lancet piercing position thereof.

19. The injector of claim 18 wherein said lancet access position is distally beyond said lancet piercing position thereof and said lancet is frictionally engageable and slidable into and out of said holder.

* * * * *